(12) United States Patent
Lahiji

(10) Patent No.: US 6,660,012 B2
(45) Date of Patent: Dec. 9, 2003

(54) APPARATUS FOR PERFORMING CIRCUMCISION

(76) Inventor: Hossein Lahiji, 1315 E. 6$^{th}$ St., Weslaco, TX (US) 78596

( * ) Notice: Subject to any disclaimer, the term of this patent is extended or adjusted under 35 U.S.C. 154(b) by 0 days.

(21) Appl. No.: 10/099,751

(22) Filed: Mar. 15, 2002

(65) Prior Publication Data

US 2003/0176872 A1 Sep. 18, 2003

(51) Int. Cl.$^7$ ............................................... A61B 17/32
(52) U.S. Cl. ....................................................... 606/118
(58) Field of Search ....................... 606/118; 227/180.1, 227/179.1

(56) References Cited

U.S. PATENT DOCUMENTS

| | | | | |
|---|---|---|---|---|
| RE20,201 E | * | 12/1936 | Sivon et al. ................ | 606/118 |
| 3,473,533 A | * | 10/1969 | Freda .......................... | 606/118 |
| 4,491,136 A | * | 1/1985 | Le Veen ...................... | 606/118 |
| 5,163,943 A | * | 11/1992 | Mohiuddin et al. ......... | 606/118 |

* cited by examiner

Primary Examiner—Michael H. Thaler
(74) Attorney, Agent, or Firm—Keaty Professional Law Corporation

(57) ABSTRACT

A circumcision instrument has two cylindrical hollow members telescopically engageable with each other. The first cylindrical member carries a sharp blade on its proximate end; the second cylindrical member has a stapling mechanism mounted inside for stapling the circumcised foreskin and reducing bleeding. The foreskin is pushed back from the head of the penis to lie against the outer wall of the first cylindrical member; then the second cylindrical member is moved to extend in part over the cut area where tissue-absorbable staples are applied.

14 Claims, 1 Drawing Sheet

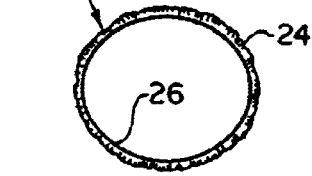
FIG. 1
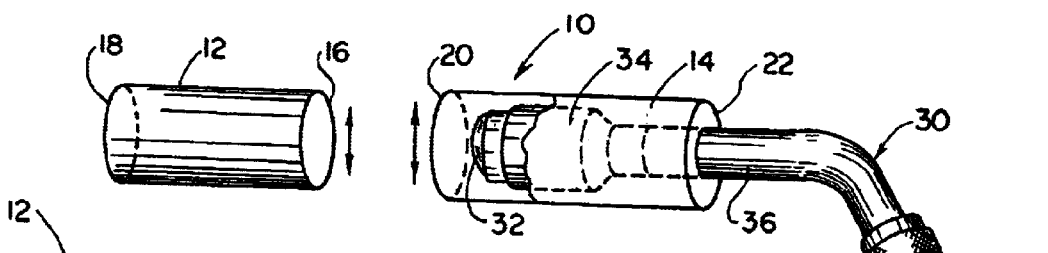
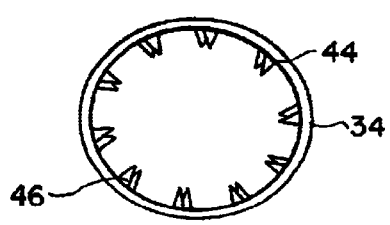
FIG. 2
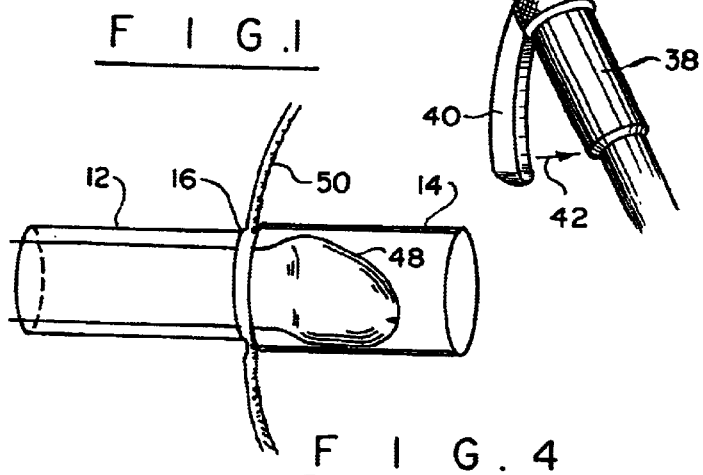
FIG. 4
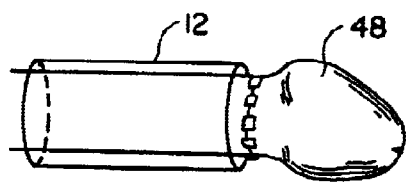
FIG. 3
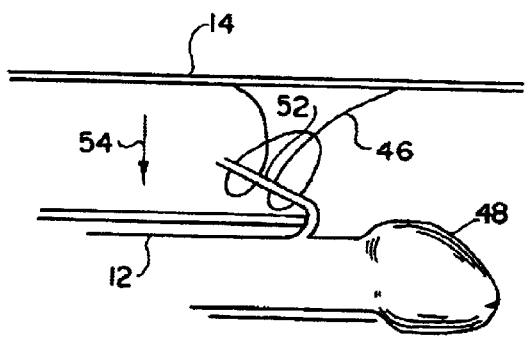
FIG. 6 FIG. 5
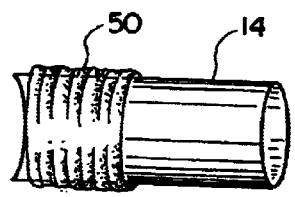
FIG. 7
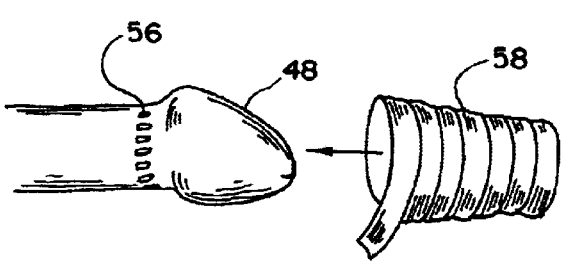
FIG. 8

APPARATUS FOR PERFORMING CIRCUMCISION

BACKGROUND OF THE INVENTION

This invention relates to a surgical apparatus and method for performing circumcisions. More particularly, this invention relates to an apparatus to facilitate the removal of excess foreskin from the penis during circumcision, while applying stitches to the cut area of the skin to reduce bleeding.

The surgical procedure of circumcision has been performed for centuries for both religious and medical reasons. Different cultures have employed various instruments for performing this procedure wherein the excess foreskin is removed. The procedure is performed on babies, as well as adults, the latter being most often performed for health reasons.

The major concern during the procedure is bleeding from the severed blood vessels and possibility of an infection. Conventional procedure normally takes about 20 to 30 minutes; a surgeon performs the incision and then applies stitches or sutures to the remaining portion of the foreskin to stop the bleeding. The more experienced and skilled the surgeon is, the less likely complications will arise following the circumcision.

The present invention contemplates elimination of drawbacks associated with prior art instruments and circumcision devices and provision of an apparatus for performing circumcisions, which will facilitate cutting and stitching of the foreskin in a rapid succession, minimizing the possibility of errors and complications in the procedure.

SUMMARY OF THE INVENTION

It is therefore, an object of the present invention to provide an apparatus and procedure for performing circumcisions.

It is another object of the present invention to provide an apparatus and procedure for removing excess foreskin from the penis while reducing the bleeding from the cut blood vessels by applying stitches to the cut surface.

It is a further object of the present invention to provide an apparatus and procedure for performing circumcision, which is simple to use and which minimizes the possibility of errors during the surgery.

These and other objects of the present invention are achieved through a provision of a circumcision apparatus and method for removing excess foreskin of a penis. The apparatus is comprised of a first and second hollow cylindrical members telescopically engageable with each other. The first cylindrical member carries an outwardly extending circular blade for severing the foreskin about a circumferential cut. The second cylindrical member has a stapling device mounted inside the hollow member.

The stapling device has a stapling mechanism located adjacent a proximate end thereof, such that the stapling mechanism is located above the area of the circumferential cut. A handle of the stapling device and an activation lever extend outwardly from the second cylindrical member, allowing a surgeon to activate the stapling action almost simultaneously with severing the foreskin (stapling is done just prior to cutting).

The stapling mechanism has a source of staples in a stapling housing unit; the staples are tissue-absorbable staples that do not require removal after the cut skin has been cut.

In operation, the excess foreskin is pushed back from the head of the penis to lie against the outer wall of the first cylindrical member, with the skin layer contacting the outer wall. The first cylindrical member is rotated to sever the excess foreskin and the stapling mechanism is activated to close the cut and push mucous and the skin layers together to reduce the bleeding.

The second cylindrical member is then withdrawn, carrying the excess foreskin away from the patient's body. A surgical dressing is applied to the cut area for a specified time, for instance two days, after which time the cut foreskin is allowed to fully heal.

BRIEF DESCRIPTION OF THE DRAWINGS

Reference will now be made to the drawings, wherein like parts are designated by like numerals, and wherein:

FIG. 1 is a perspective view of the circumcision apparatus in accordance with the present invention.

FIG. 2 is a detail end view of the first cylindrical member forming part of the apparatus of the present invention.

FIG. 3 is a detail end view of the second cylindrical member of the present invention showing a stitching mechanism at the end of the second cylindrical member.

FIG. 4 is a schematic view illustrating the first step in the procedure of the present invention.

FIG. 5 is a schematic view showing stitches applied to the cut skin at the surgical site.

FIG. 6 is a detail view showing the position of the stitches.

FIG. 7 is a detail view showing the second cylindrical member being removed with the severed excess foreskin.

FIG. 8 is a schematic view showing location of the applied stitches right before application of a surgical dressing.

DETAILED DESCRIPTION OF THE PREFERRED EMBODIMENT

Turning now to the drawings in more detail, numeral 10 designates the apparatus of the present invention. The apparatus 10 comprises a first cylindrical member 12 and a second cylindrical member 14. The cylindrical members 12 and 14 are hollow, with a diameter of the first cylindrical member 12 being slightly smaller than the diameter of the cylindrical member 14.

The first cylindrical member 12 has a proximate end 16 and a distal end 18. The cylindrical member 14 has a proximate end 20 and a distal end 22. The proximate end 16 of the first cylindrical member 12 is provided with a sharp blade 24 facing outwardly from the interior wall 26 of the first cylindrical member 12, as can be seen in FIG. 2.

The second cylindrical member 14 houses a stitching device 30 which has an anvil head assembly 32, a staple housing unit 34, and a shaft 36 secured to the staple housing 34. The staple housing 34 houses a plurality of intraluminal staples that can be safely applied to the human skin. It is preferred that the staples be tissue-absorbable staples that may be left in the skin to be fully absorbed by the skin.

The opposite end of the shaft 36 carries a stationary handle 38 and a hinged lever 40. The lever 40 is operationally connected to the staple mechanism through the shaft 36. When pressure applied to the lever 40 in the direction of arrow 42, the stapling mechanism is activated causing staples located in the staple housing unit 34 to be ejected and applied to the skin, as will be described in more detail hereinafter.

The staples are housed in the staple housing unit 34 adjacent to the proximate end 20 of the second cylindrical member 14. The stitching mechanism 44 (FIG. 3) is a conventional intraluminal stapler mechanism, wherein staples are 46 are equidistantly distributed about the circumference of the stitching mechanism, as can be better seen in FIG. 3. It is envisioned that 12 to 16 stitches are sufficient to arrest bleeding from severed blood vessels.

Turning now to FIGS. 4–8, the method of using the apparatus 10 and the procedure of the present invention will now be described in more detail.

A surgeon positions the first cylindrical member 12 in a covering relationship over the head of the penis 48, with the proximal end 16 being positioned at a location where the circumferential cut is to be performed. The surgeon may then cuts the foreskin 50 longitudinally allowing the excess foreskin to be pushed away from the head of the penis 48. The surgeon then moves the second cylindrical member 14 over the head the penis 48, pushing the foreskin 50 away, as shown in FIG. 4. The foreskin may be pushed further so that the skin layer of the foreskin lies almost flat against the outer wall of the first cylindrical member 12.

The first cylindrical member 12 is then rotated, causing the blade 24 to cut into the foreskin 50 and create a circumferential cut. The removed excess foreskin 50 becomes positioned on the exterior wall of the second cylindrical member 14, as shown in FIG. 7. Next, the surgeon compresses the lever 40, causing the staples 46 to be ejected from the staple housing unit 34 to the foreskin 52 (FIG. 5) that remains attached to the penis. The foreskin 52 has an inner mucous layer and an outer skin layer that must be stitched and clamped together to stop the bleeding from the severed blood vessels.

The staples 46 are applied about the entire circumference of the foreskin 52, forming multiple stitches on the foreskin 52. The surgeon may move the second cylindrical member 14 against the outer wall of the first cylindrical member 12, in the direction of the arrow 54 (FIG. 5) to totally close and tie the applied stitches. The staples 46 are fully absorbable by the human tissue and need not be removed.

The surgeon then removes the second cylindrical member 14 and slides the first cylindrical member 12 away from the penis, leaving a plurality of stitches 56 formed about the circumference of the cut tissue.

A conventional sterile dressing 58 may then be positioned over the stitches 56 to allow for healing of the surgical site in a sterile environment. After several days of healing, the dressing 58 can be removed and discarded. The stitches 56 will disintegrate and become absorbed into the body, minimizing the need for doctor's visits and follow-up care.

In comparison with conventional methods, the apparatus of the present invention allows to perform the circumcision procedure much faster, in the matter of 2–3 minutes, with considerably less discomfort and trauma to the patient.

The stitching unit of the present invention may be modified, eliminating the anvil head 32 and using the outer wall of the first cylindrical member 12 as the anvil when the foreskin is folded over the first cylindrical member 12, with the first cylindrical member 12 serving as an area against which the staples may be compressed and secured on the foreskin.

Many other changes and modifications can be made in the apparatus and process of the present invention without departing from the spirit thereof. I, therefore, pray that my rights to the present invention be limited only by the scope of the appended claims.

I claim:

1. A circumcision apparatus for removing foreskin from the penis, comprising:
   a first hollow cylindrical member and a second hollow cylindrical member telescopically moveable in relation to the first cylindrical member and engaging foreskin between an inner wall of the second cylindrical member and an outer wall of the first cylindrical member;
   a means carried by said first cylindrical member for performing a circumferential cut in the foreskin while said first cylindrical member is rotated; and
   a means carried inside by said second cylindrical member for stapling and closing the foreskin about the line of the circumferential cut.

2. The apparatus of claim 1, wherein said second cylindrical member has an inner diameter greater than an outer diameter of said first cylindrical member.

3. The apparatus of claim 1, wherein said means for performing a circumferential cut comprises a blade extending outwardly from a proximate end of the first cylindrical member.

4. The apparatus of claim 1, wherein said means for stapling comprises an intraluminal stapling device positioned in said second cylindrical member, said stapling device comprising a stapling mechanism for applying tissue absorbable staples to the area of the circumferential cut.

5. The apparatus of claim 4, wherein said stapling device further comprises a handle extending outside of said second cylindrical member and a means for activating said stapling mechanism.

6. The apparatus of claim 4, wherein said stapling mechanism is sized and configured to extend about an interior circumference of a proximate end of said second cylindrical member for applying the staples about an entire circumferential area of the circumferential cut simultaneously.

7. The apparatus of claim 1, wherein said second cylindrical member telescopically engages said first cylindrical member and presses the foreskin against the outer wall of said first cylindrical member.

8. A circumcision apparatus for removing foreskin from the penis, comprising:
   a first hollow cylindrical member and a second hollow cylindrical member telescopically moveable in relation to said first cylindrical member and engaging foreskin between an inner wall of the second cylindrical member and an outer wall of the first cylindrical member, said second cylindrical member telescopically engaging said first cylindrical member;
   a blade carried by said first cylindrical member for performing a circumferential cut in the foreskin while the first cylindrical member is rotated, said blade extending outwardly from a proximate end of said first cylindrical member; and
   a means carried inside by said second cylindrical member for stapling and closing the foreskin about the line of the circumferential cut.

9. The apparatus of claim 8, wherein said means for stapling comprises an intraluminal stapling device positioned in said second cylindrical member, said stapling device comprising a stapling mechanism for applying tissue absorbable staples to the area of the circumferential cut.

10. The apparatus of claim 9, said stapling mechanism is configured to extend about an interior circumference of a proximate end of said second cylindrical member for applying the staples about an entire circumferential area of the circumferential cut simultaneously.

11. The apparatus of claim 9, wherein said stapling device further comprises a handle extending outside of said second cylindrical member and a means for activating said stapling mechanism.

12. A method of reducing bleeding from cut foreskin during circumcision of a penis, comprising the following steps:

provuding a first hollow cylindrical member and a second hollow cylindrical member;

positioning said first cylindrical member about the head of the penis, with a proximate end of the first cylindrical member extending about a pre-selected circumcision area;

positioning the second cylindrical member in telescopic engagement over the proximate end of the first cylindrical member and pushing a skin layer of the foreskin against an outer wall of the proximate end of the first cylindrical member;

providing a blade on the proximate end of the first cylindrical member;

rotating the first cylindrical member, while performing a circumferential cut in the foreskin, and while severing excess foreskin;

providing a stapling means in said second cylindrical member;

then stapling the foreskin along the cut line to close mucous and skin layers and reduce bleeding; and then removing severed excess foreskin.

13. The method of claim 12, wherein said step of stapling the foreskin comprises a step of applying tissue-absorbable staples to the cut foreskin.

14. The method of claim 12, wherein said step of providing the stapling means comprises a step of providing a stapling device with a stapling mechanism mounted adjacent a proximate end of said second cylindrical member, said stapling mechanism being activated by a compression of a lever extending outside of said second cylindrical member.

* * * * *